United States Patent [19]

Sozio et al.

[11] Patent Number: 4,585,417

[45] Date of Patent: Apr. 29, 1986

[54] DENTAL APPLIANCE AND METHOD OF MANUFACTURE

[75] Inventors: Ralph B. Sozio, Boston; Edwin J. Riley, Milton, both of Mass.

[73] Assignee: Coors Porcelain Company, Golden, Colo.

[21] Appl. No.: 612,436

[22] Filed: May 21, 1984

Related U.S. Application Data

[63] Continuation of Ser. No. 378,969, May 17, 1982, abandoned, which is a continuation-in-part of Ser. No. 103,647, Dec. 14, 1979, abandoned.

[51] Int. Cl.$^4$ .................. A61C 5/08; A61C 13/083; B29C 33/52

[52] U.S. Cl. .................. 433/202.1; 264/19; 264/221; 264/314; 264/317; 264/328.18; 264/338; 264/DIG. 44; 433/212.1; 433/218; 433/222.1; 433/223

[58] Field of Search .............. 264/19, 221, 314, 317, 264/328.18, DIG. 44, 338; 433/203.1, 202.1, 212, 218, 222.1, 223

[56] References Cited

U.S. PATENT DOCUMENTS

| | | |
|---|---|---|
| 1,372,772 | 3/1921 | Nishi . |
| 2,000,285 | 5/1935 | Hoffmann . |
| 2,118,934 | 5/1938 | Madzar ........................... 433/222.1 |
| 2,194,790 | 3/1940 | Glück ............................. 433/223 X |
| 2,317,008 | 4/1943 | Werner .......................... 264/221 X |
| 2,317,103 | 4/1943 | Meier . |
| 2,696,667 | 12/1954 | Saccai ............................ 433/222.1 |
| 3,052,983 | 9/1962 | Weinstein et al. ............. 433/223 X |
| 3,069,773 | 12/1962 | Saffir ............................. 433/202.1 |
| 3,090,691 | 5/1963 | Weyer . |
| 3,181,240 | 5/1965 | Kerhart et al. ................. 433/203.1 |
| 3,229,003 | 1/1966 | Bowman ........................ 264/19 |
| 3,238,048 | 3/1966 | Somers . |
| 3,413,724 | 12/1968 | Segal . |
| 3,464,837 | 9/1969 | McLean et al. ............. 433/202.1 X |
| 3,516,810 | 6/1970 | Ivey et al. ..................... 65/33 |
| 3,532,776 | 10/1970 | Kopp ............................. 264/19 |
| 3,549,393 | 12/1970 | Elarde . |
| 3,636,632 | 1/1972 | Costa et al. .................. 32/5 |
| 3,716,418 | 2/1973 | Kochavi ....................... 148/6.3 |
| 3,766,650 | 10/1973 | Gnecco ......................... 433/202.1 |
| 3,880,662 | 4/1975 | Daskalon et al. ............. 433/202.1 X |
| 3,934,348 | 1/1976 | Janjie ........................... 433/222.1 |
| 4,040,844 | 8/1977 | Gnecco ......................... 433/202.1 |
| 4,105,456 | 8/1978 | Murakami et al. ............ 428/428 X |
| 4,115,488 | 9/1978 | Colpitts ........................ 264/19 X |
| 4,155,964 | 5/1979 | Aronow ........................ 264/19 X |
| 4,265,669 | 5/1981 | Starling et al. ................ 264/65 X |

OTHER PUBLICATIONS

Riley, Edwin J.; Ralph B. Sozio; Franklin Casthely; M. Thomas Wilcko and Alfred J. Sotera, "Precision Porcelain Jacket Crown Technique," in *Journal Prosthetic Dentistry*, vol. 34, No. 3, Sep., 1975, pp. 346-351.

*Primary Examiner*—Philip Anderson
*Attorney, Agent, or Firm*—Reising, Ethington, Barnard, Perry & Milton

[57] ABSTRACT

A tooth crown or the like fixed, custom fitted dental appliance made of a fired ceramic which undergoes substantially no shrinkage when fired, the appliance being made by forming a compact of the raw prefired ceramic with an undersurface shaped for a precise fit onto the prepared tooth on which the appliance is to be used, and thereafter firing the compact to a dense hard monolithic structure.

13 Claims, 4 Drawing Figures

DENTAL APPLIANCE AND METHOD OF MANUFACTURE

This is a continuation application of U.S. application Ser. No. 378,969, filed May 17, 1982, now abandoned which was a continuation-in-part application of U.S. application Ser. No. 103,647, filed Dec. 14, 1979 and now abandoned.

TECHNICAL FIELD

This invention relates to a method for the fabrication of dental appliances such as crowns, bridges and the like, and to dental appliances made by such method.

For simplicity, the invention and its background will herein be principally with reference to tooth crowns and their manufacture, though it will be understood that the invention has application to other dental appliances such, for example, as dental bridges.

BACKGROUND ART

A dental crown is one of the most important restorations in dentistry in that it affords the restoration of deteriorated teeth to a state of health and function. One of the prime requisites for a successful dental crown is that it adapt as perfectly as possible to the prepared tooth structure (i.e. the tooth is milled to a desired shape upon which the dental crown is placed). Anything less than substantially perfect fit, especially at the crown margin, can result in mechanical failure such as crown fracture or loosening or biologic failure such as decay, periodontal disease, or occlusal problems. At the present state of the art the materials available for the fabrication of crowns include the noble metals such as gold base alloys, acrylics such as polymethyl methacrylate, dental porcelain, or a composite of a metal and a compatible porcelain or acrylic.

At the present date the most widely employed method of fabricating dental crowns is to cast a metal substrate which is subsequently covered with a dental porcelain veneer.

The metal substrate is obtained by an indirect process known as the "lost wax" technique. Specifically, the substrate is first formed and shaped in wax. This involves making an impression of the prepared tooth, casting dental stone against the impression to form a master die, molding a body of wax against the master die and then shaping the upper portions of the wax body to duplicate the external shape of the tooth crown desired. The wax form must then be accurately converted to the metal. To accomplish this the wax form is invested into a refractory material, thus forming a mold. The wax is then eliminated by melting or burning, thus creating a cavity into which the metal, heated to a molten state, is cast. Hence, the wall of the cavity intended to be an exact replica of the prepared tooth can suffer inaccuracies because of the three-step technique needed to prepare it—preparation of the master die, preparation of the wax form from the master die, and preparation of the mold from the wax form. This renders the process technique-sensitive. The process is even further technique-sensitive in that each metal alloy possesses a specific casting shrinkage for which there must be accurate compensation. This compensation is critically dependent upon the proper selection and skillful manipulation of all materials employed. The technique is sensitive in that failure can occur at any of the numerous steps involved, such as distortion of the wax form, improper investing procedure, inadequate expansion of the mold, improper burn-out procedure, or improper melting and casting of the metal. A principal drawback of this technique is that many hours are consumed before a failure in the casting stage can be detected. The success or failure of the composite ceramic-metal crown is also greatly dependent on the proper finishing and handling of the surface of the metal to which the ceramic is applied. Proper finishing which is difficult and time consuming, is essential to the successful bonding of the ceramic to the metal substrate. Still further, the inherent physical differences between the porcelain veneer and the metal substrate, such as differences in thermal expansion, give rise to numerous potential avenues for failure.

An alternative technique, which eliminates the need for a metal casting, is to form the crown of a dental porcelain with a thin underlayer of platinum foil. The thin platinum foil is carefully shaped to a replica of the prepared tooth and the dental porcelain is then overlaid onto the foil which supports the porcelain during the subsequent firing cycles necessary. This procedure is extremely technique-sensitive, requiring skillful and meticulous processing. Proper and accurate shaping of the platinum foil over the replica is extremely difficult and frequently leads to poorly fitted crowns. Additional problems of fit arise due to the shrinkage of the dental porcelain which often distorts the thin platinum matrix during firing. It is therefore more difficult to obtain the desired fit with this crown as compared to the cast metal porcelain composite.

DISCLOSURE OF THE INVENTION

The present invention provides a dental appliance which has excellent strength, durability, density, appearance and fit but yet which can be made at relatively low cost both by reason of the material used and, even more significantly, by reason of simplified processing. In accordance with the invention, the tooth crown or other dental appliance has a tooth-engaging substrate formed of a shrink-free ceramic. Where, as is generally the case, it is desired that the appliance have greater translucence and closer color match to that of the natural tooth, the substrate is coated on its outer surfaces with a porcelain or glaze veneer having the color and degree of translucency desired.

A preferred shrink-free ceramic for the practice of the invention will be described in detail hereinafter; however, suffice it to say at this point that by the term "shrink-free ceramic" is meant a ceramic made from a ceramic powder formulation which, when compacted and then fired to maturity, converts to a dense, hard, monolithic body which has the same volume and shape as were the volume and shape of the ceramic powder compact prior to firing. Because the ceramic does not undergo shrinkage when fired to maturity, i.e. to high strength and hardness, the powder compact can, prior to firing, be formed to the identical size and shape desired for the crown or other appliance with complete assurance of the required perfect fit to the prepared tooth to which it is to be secured. And because the ceramic powder can be readily molded at relatively low temperature into a compact of any desired shape and with the resulting compact itself being relatively soft such that portions thereof can be easily removed for any further shaping as might be required, the invention provides much simplified processing for dental crowns or other appliances having the required perfect fit along with high strength and all other desired characteristics.

Fundamentally, the method of the present invention involves only three essential steps, namely: (1) preparation of a die which is an exact replica of the prepared tooth to which the crown or other dental appliance is to be fitted; (2) molding or otherwise forming a compact of the raw particulate shrink-free ceramic against the die and simultaneously, or thereafter, shaping the remaining surface portions of the compact to the shape and size desired for the appliance; and (3) firing the so-shaped compact to its maturing temperature. As a last step, generally necessary for purposes of matching the appearance of the natural tooth, the fired shrink-free ceramic substrate, so manufactured, is coated with a suitable porcelain veneer or glaze thereby completing preparation of the appliance which is thereafter secured to the prepared tooth.

As will be discussed in greater detail hereinafter, the die is prepared by taking an impression of the prepared tooth and then preparing the die by use of the impression, the die being of a material having sufficient strength and other physical characteristics to render it suitable for molding the raw ceramic thereagainst in the molding step which follows. Then, a mold is prepared with the die as a wall portion thereof. To this end wax (which can be a wax such as paraffin or some other material which can be easily melted or vaporized) can be molded against the die, after which the remaining surfaces of the resultant wax body can be shaped to duplicate the external crown shape desired. Dental stone or the like is then cast against the wax body thereby to form a mold in which the die serves as the mold wall intended to be an exact replica of the prepared tooth. Mold preparation is completed by melting or burning out the wax. Such mold is then used for fabricating the shrink-free ceramic to the crown shape desired. Hence, the surface portion of the crown which fits against the prepared tooth is formed by shaping it against the die rather than against a mold wall consisting of an investment surface prepared from a wax body shaped by molding the wax against the die. This greatly increases the closeness and accuracy of fit of the crown to the prepared tooth and it is enabled by the fact that the shrink-free ceramic can be shaped at low temperature, as compared with the temperatures required for casting metal.

In the preferred method as just described, the entire final shape of the shrink-free ceramic compact is accomplished simultaneously with the shaping of that portion of the compact which, after firing, is to fit against the prepared tooth. However, it is within the purview of the invention to form the non-tooth engaging portions of the compact to the final desired shape subsequent to forming the compact against the die. That is, the wax body formed against the die can, if desired, be shaped on its external surfaces only roughly to the external shape desired of the compact, leaving it for further and final shaping of such surfaces of the compact after it has been molded. As has already been mentioned, such final shaping of the powder compact is relatively simple, since the compact is soft and hence easily sculptured prior to firing.

The above and other features and advantages of the invention will appear more clearly from the detailed description of preferred embodiments which follows.

BEST MODE FOR CARRYING OUT THE INVENTION

Figure 1:
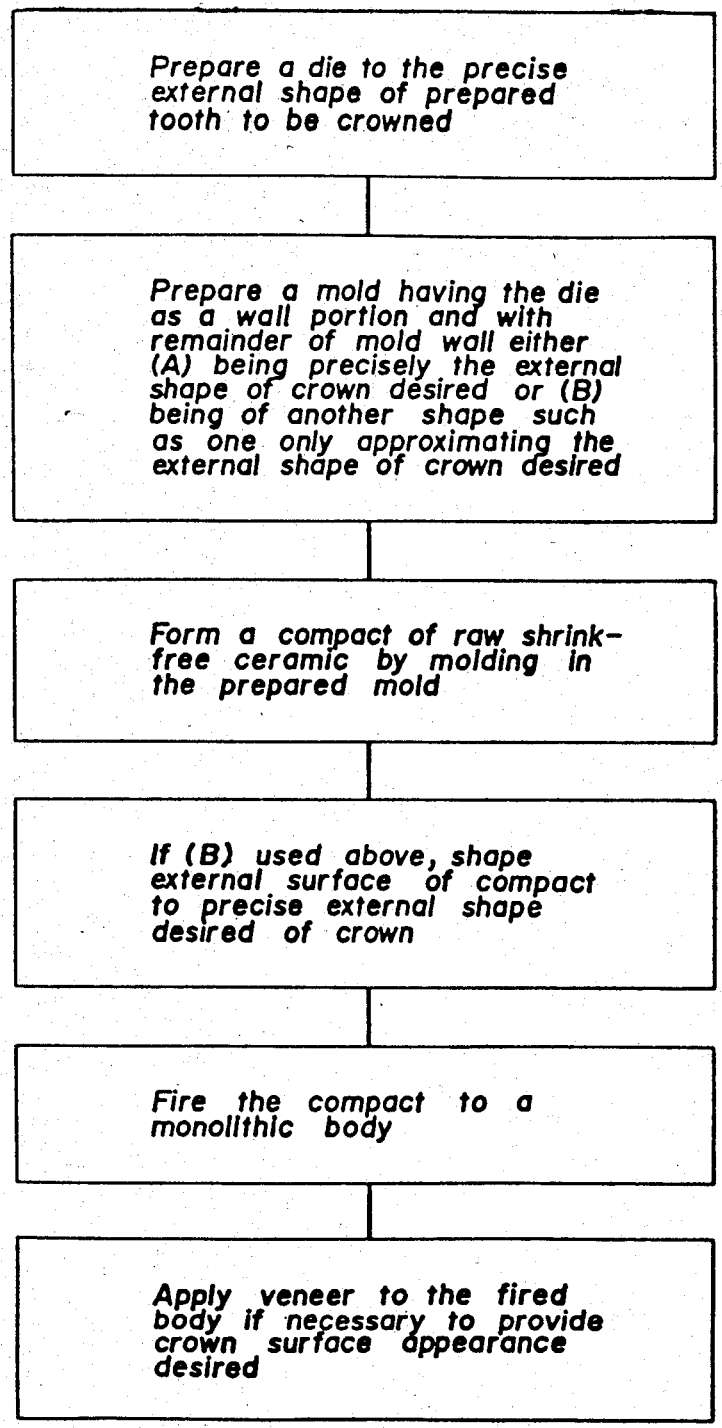
FIG. 1 is a flowchart showing steps involved in the practice of a preferred embodiment of the invention.

As has already been made clear, a key feature of the present invention is the use of shrink-free ceramic as the material for the dental appliance substrate. Various shrink-free ceramics have been proposed for use as industrial ceramics but before further discussing them, it is appropriate to mention briefly some of the characteristics of more conventional ceramics and and their manufacture.

Conventional ceramic bodies, typically alumina ceramics, are manufactured by forming a raw batch of the desired ceramic ingredients in particulate form, (e.g. aluminum oxide) plus a binder, molding or otherwise forming the raw batch into a compacted body, and then firing the compacted body to sinter or vitrify the ceramic.

During the firing operation there is considerable linear shrinkage—generally from about 10% to 20%—which means that the compact must be made larger than the desired fired body. Also, because shrinkage is never exactly uniform throughout the body, there is always a certain amount of warpage or distortion—though with good quality control it is generally possible to maintain warpage or distortion within the bounds of normal tolerances for electrical insulators, mechanical components and the like industrial ceramic bodies.

Shrinkage occurs for one of a combination of two reasons. First, no matter that even high pressure is used to mold or otherwise form the compact, the density of the compact is not as high as theoretically possible—there is always some porosity—to the end that there is some shrinkage when the compact fires to a high density non-porous monolith. The use of an organic binder in the compact, which is generally desirable to add green strength, may contribute to the porosity of the compact since it is vaporized or burned out during the subsequent firing operation to mature the ceramic to dense monolithic structure. Secondly where the ceramic ingredients undergo chemical or crystalline transformation during the firing, if the ceramic formed is of greater density and lesser volume than the raw ceramic ingredients, then this also contributes to the shrinkage.

Generally, reason (1) cannot be entirely eliminated even for the manufacture of shrink-free ceramic bodies. However, in the case of most shrink-free ceramic bodies, the formulation of raw particulate ceramic ingredients is one wherein one or more of the ingredients undergo either chemical or crystalline transformation during the firing and with the resultant ceramic formed by way of the chemical or crystalline transformation occupying a greater volume than that of the raw ingredients, to the end that this increase in volume exactly compensates for the decrease in volume caused by reason (1). Hence, for example, it is known that kyanite converts to mullite and silica upon firing, the combined volumes of the mullite and silica being greater than the volume of the kyanite. Accordingly, it is known to formulate a ceramic batch of kyanite, generally along with other ceramic ingredients, the amount of kyanite being such as to produce, during firing, a volume increase sufficient to compensate for the shrinkage which would otherwise occur by reason of the inclusion of binder and the relatively high porosity of the compact prior to firing. Various and diverse examples of shrink-free ceramics are discussed in the article entitled "Porcelains Having Low-Firing Shrinkage", Volume 43, No. 5 (1964) Ceramic Bulletin of the American Ceramic Society. U.S. Pat. No. 3,549,393 Elarde also discloses such ceramics.

In addition to being shrink-free the ceramic used in the practice of the invention should have high flexural strength (preferably above 15,000 psi), high compression strength (preferably above 50,000 psi), low porosity and commensurately high density (preferably above 80% of the theoretically highest density possible for the ceramic used), and a low coefficient of thermal expansion (preferably below $8.0 \times 10^{-6}$°/C.). To provide the desired strength and hardness it is preferred that the ceramic be an alumina ceramic, i.e. a fired ceramic made from a formulation containing, as its ceramic ingredients, more than 50% by weight aluminum oxide and hence showing on chemical analysis, expressed in terms of single oxides, more than 50% by weight aluminum oxide.

The preferred shrink-free ceramic, and processing thereof, for the practice of the present invention is that set forth in U.S. patent application Ser. No. 103,771 filed Dec. 14, 1979, now U.S. Pat. No. 4,265,669, in the names of Lynn B. Starling, James E. Stephan, and Robert D. Stroud. Such shrink-free ceramic body utilizes the fact that when aluminum oxide and magnesium oxide combine, during firing, to form magnesium aluminate spinel (MgO $Al_2O_3$) there is a volume increase which compensates for the shrinkage which would otherwise occur. Also, in this preferred shrink-free ceramic the binder used is a silicone resin containing a high percentage (upwards of about 50% by weight) SiO groups to the end that upon binder burnout during firing, a major portion thereof remains in the resultant ceramic body as silica or silicate.

The following is the most preferred batch formulation for such shrink-free ceramic:
$Al_2O_3$ (particle size, 0.4 to 10 microns—average 2.5 microns): 100 grams
$Al_2O_3$ (−325 mesh, Tyler): 40 grams
$BaO.SiO_2.Al_2O_3$ glass (53% BaO, 42% $SiO_2$, 5% $Al_2O_3$): 30 grams
MgO (−200 mesh, Tyler): 20 grams
Edgar plastic kaolin: 9 grams
Calcium stearate: 2 grams
Acrawax C (steryl amide, wax, melting temperature 290° F.): 2 grams
Silicone resin: 28 grams The variated particle size of the ceramic batch is to provide high compaction density. The calcium stearate and Acrawax function as lubricants during the compaction operation. When the above body is fired to a temperature of about 1300° C., the magnesia and some of the alumina combine to form the spinel, and other of the ingredients, including silica from the silicone resin, form a glassy phase, the resultant matured body being possessed of a high density (approximately 2.7 g/cc.), excellent physical strength (flexural strength upwards of 15,000 psi; compression strength upwards of 50,000 psi) and a low coefficient of thermal expansion (below $6.0 \times 10^{-6}$°/C.). During the firing there is no shrinkage, and in this regard it is desirable to fire the ceramic on a gradual schedule, for example, by first gradually heating to about 500° C. and holding the body there for about 2 hours, and thereafter gradually raising the temperature, over a period of about 9 hours, to 1300° C.-1320° C., preferably with a hold of about ½ hour at this highest firing temperature. By way of the gradual heating, escape of SiO groups from the silicone resin is inhibited to the end that substantially all of the SiO groups of the silicone resin remain in the fired body as silicate.

As discussed in the aforementioned U.S. Pat. No. 4,265,669, variations from the above formulation can be used, the key ingredients in the preferred formulation being the alumina and magnesia, the glassy or glass-forming ingredients to provide a glassy phase; and silicone resin having a high percent of SiO groups—upwards of 50%—to function as the binder.

It will be also understood that whereas the aforedescribed ceramic has, to date, been found to be best and hence is most preferred, other shrink-free formulations can be used for the practice of the invention.

Reference is now made to the flowchart shown in FIG. 1.

The first step involves preparation of the die to the precise shape of the prepared tooth. It is necessary that the die be formed of a material having sufficient strength and other physical characteristics to be suitable for molding thereagainst the raw ceramic in the molding operation in which the die is used as a wall of the mold. The preferred material for the die is an epoxy resin which cures to high strength and hardness and which either undergoes no shrinkage during cure or, if it does, can be restored to its as-cast dimensions. Also, if the raw ceramic is to be molded in a heated condition, the die material should have a coefficient of thermal expansion the same or quite similar to that of the raw ceramic. The preferred material for the die, and the preferred manner of using such material, is disclosed in U.S. patent application Ser. No. 310,170 filed Oct. 9, 1981 in the names of James E. Stephan, Paul A. Boduch and John A. Elverum and assigned to the assignees of the present invention. Such material is a castable liquid epoxy resin formulation having, as its most preferred embodiment, Component A consisting essentially of about 52% by weight epoxy novolac polymer wherein the average number of intermediate repetitive groups is from 0.2 to 1.8, about 40% by weight vinyl -3-cyclohexane diepoxide and about 8% by weight 3,4 epoxy cyclohexylmethyl -3,4-epoxy cyclohexane carboxylate, and Component B consisting essentially of partially hydrolyzed pyromellitic acid dianhydride containing at least about 90% by weight of the dianhydride. In the preferred embodiment a tertiary amine catalyst is also included in an amount up to about 0.06 parts by weight for each part by weight of combined Components A and B. These components are mixed, just before use, in a ratio of from 30 parts by weight Component B to each 100 parts by weight Component A and the mixture then cast in the impression and allowed to cure to a solid body while in the impression. Slight shrinkage occurs during curing; however by thereafter heating the resulting die preferably at a rate of from about 5° C. to 25° C. per minute up to from 140° C. to 160° C. it can, by the amount of hold time at such temperature, be caused to undergo permanent expansion until it is restored precisely to its as-cast dimensions. Such epoxy resin is particularly desirable as the die material where the shrink-free ceramic used is of the preferred formulation hereinafter disclosed wherein silicone resin is an ingredient and where the molding of the raw ceramic is by the preferred molding operation hereinafter disclosed wherein the raw ceramic is molded at a temperature sufficient to soften the silicone resin so that it provides the raw ceramic thermoplastic properties during molding and functions as a binder. To commence the dental procedure, the dentist prepares the tooth to be crowned by removing enough of the tooth structure to allow proper thickness of the final crown, after which the dentist secures a negative of the prepared tooth with a suitable impression material, all of which can be in accordance with conventional practice. The die which is to be used as the mold wall for molding the raw ceramic is then prepared, preferably by casting the epoxy or other material of which the die is to be constructed in the impression of the prepared tooth. As an alternative method: (a) a model of the prepared tooth is made by casting a material such as dental stone into the impression; (b) after the tooth model hardens and is removed from the impression, an impression is made of the tooth model; and (c) the material of which the die is to be constructed is then cast in this impression of the tooth model. Though the alternative method is quite satisfactory for the practice of the invention the preferred method is advantageous in that it best assures that the die will be an exact replica of the prepared tooth. However, the preferred method cannot be used if the impression material used by the dentist for securing the impression of the prepared tooth is not suitable for casting thereagainst the material of which the die is to be formed. Specifically, if the die is to be formed of an epoxy resin such as the preferred epoxy formulation indicated above, and if the dentist uses a water-containing hydrocolloid type impression material (well known in the dental art) for securing the impression of the prepared tooth, then the preferred method cannot be used since such type of impression material is not satisfactory for casting thereagainst such an epoxy resin formulation for forming the die. In that case the alternative method can be used since such an impression material is satisfactory for casting a material such as dental stone for making a tooth model, an impression then being taken of the tooth model in an impression material which is satisfactory for casting the epoxy formulation for forming the die. An impression material (also well known in the dental art) of the synthetic elastomeric type (whether it be of polyether, silicone, polysulfide or vinyl polysiloxane elastomer, all commonly used) is excellent for casting such an epoxy formulation. Hence, if the dentist uses a synthetic elastomeric type impression material to secure the impression of the prepared tooth, the preferred method of preparing the die can be used.

After the die is prepared it is related to a model of the opposing arch (upper to lower teeth) on an articulator which simulates jaw movements. When the die at this stage is of multiple teeth, the dies for the individual teeth to be crowned are then separated by fine saw blades to allow easy manipulation of the dies and then trimmed, i.e. ditched, such that the margins (the exact point where the crown is to end) are visible and accessible, all as well known in the dental art.

Figure 2:
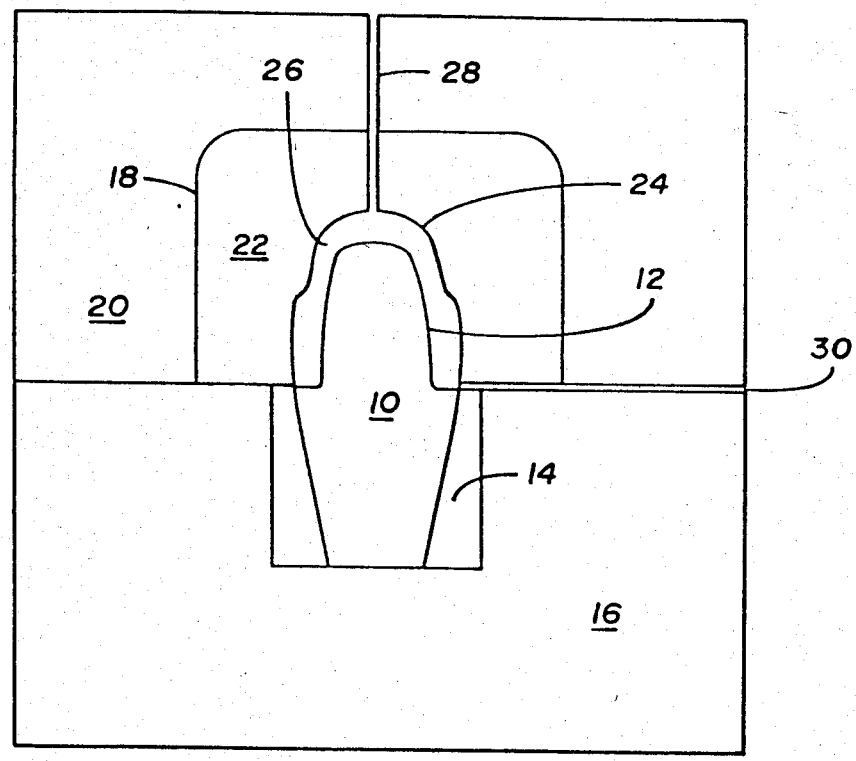
FIG. 2 is a schematic view of molding apparatus for practice of the preferred embodiment.

Next the die, duplicative of the tooth to be crowned, is secured to form a portion of a mold for the molding of the shrink-free ceramic raw batch. Reference is made to FIG. 2 which depicts such a mold. In FIG. 2, 10 is the die the outer surface 12 of which is duplicative of the prepared tooth to be crowned and the lower portion of which is simply a base set into an anchoring material 14, such as gypsum, within a recess in a lower mold block 16. Within a recess 18 in an upper mold block 20 is a female mold 22 the inner surface 24 of which defines, in combination with the die, the mold cavity 26 for molding the shrink-free ceramic formulation. An opening 28 is provided for admission of the shrink-free ceramic formulation into the mold and a second opening 30 can be provided as a vent for the escape of air during the admission. To simplify the mold structure, vent 30 can, if desired, be eliminated since the mold cavity is relatively small and the porosity of the investment material of the female mold is sufficient to receive the amount of air in the cavity. Prior to use of the mold for molding the shrink-free ceramic there is applied to the surface of the die a film of a suitable mold release agent such as stearic acid or a polyflurocarbon such as polytetrafluoroethylene to assure easy release of the molded raw ceramic compact from the die after the mold is disassembled. By applying the film to a thickness equal to that desired for the film of cement to be used to secure the final crown to the prepared tooth, the recess of the resulting compact, and hence also of the crown after firing, is of precisely the size to accommodate the film of cement of such thickness when the crown is fitted onto and bonded to the prepared tooth. Hence, the film of release agent can be used to serve a dual function.

Cardinal to the invention is that a shrink-free ceramic formulation be shaped against the die under sufficient pressure to assure complete conformity of the shrink-free ceramic formulation to the die. It is desirable, though not essential to the practice of the invention in its broadest scope, to accomplish this by a molding operation wherein the mold shape is such that the the outer surfaces of the substrate which is molded are of the final shape desired. This involves preparation of the female mold to provide such shape and this can be accomplished by the use of a "lost wax" technique. That is, an expendable material which can subsequently be easily converted to a fluid state, typically a wax such as paraffin, is applied over the surface of the die (after application of the film of release agent thereto) and built up and sculptured to provide a wax coping with an external shape the same as desired for the ceramic substrate after which an investment material, such as gypsum, is cast against the wax and allowed to set to hardness. The assembly is then heated to melt or burn out the wax coping.

Particularly where the mold is so prepared so as to mold the shrink-free ceramic formulation to the final shape desired for the substrate, it is preferred that the molding operation be one of transfer molding, as set forth in the aforementioned U.S. Pat. No. 4,265,669. Briefly, the method involves the preparation of a preform of the compacted shrink-free ceramic formulation, this pre-form being thereafter heated sufficiently to where it is flowable and the material thereof transferred by pressure into the mold. Just as is true of compression molding and injection molding, either of which can be used for the practice of the invention, transfer molding is broadly well-known in the plastics molding art. In this regard, it should be mentioned that where the binder used in the shrink-free ceramic formulation is a silicone resin, the overall formulation can be considered, for purposes of molding, as a highly filled organic polymer, and since silicone resin softens prior to curing, it can be either compression molded at a temperature to cause it to cure or it can be injection molded at a lower temperature at which it remains a thermoplastic. Where the preferred shrink-free ceramic formulation specified above is used and is formed into a compact by molding, it is quite satisfactory to use a molding temperature of about 150° C. and mold at a pressure of about 500 psi.

The molding can also be accomplished by the so-called isostatic molding technique which is well known in the industrial ceramics manufacturing art and which is really more in the nature of a cold pressing operation. Briefly, isostatic molding involves the use of an elastomeric mold to which hydraulic or the like external pressure is applied thereby to compress and compact the ceramic raw batch contained therein into a self-sustaining compact. This is satisfactory if the raw shrink-free ceramic formulation used is such that it can be molded at or near room temperature, in which case the die need not meet the same heat resistance and other physical requirements met by the preferred epoxy resin die material, to the end that the die can be of such materials as dental stone or the like. However, where, as in the preferred ceramic, the formulation includes silicone resin to function as the binder, it is necessary that the isostatic molding be at a temperature sufficient to soften the silicone resin.

As has been alluded to earlier herein, it is not necessary to the practice of the invention, in its broadest scope, to mold the shrink-free ceramic formulation to the precise external shape desired for the substrate but rather it is only necessary to mold the tooth engaging portion thereof (i.e. the portion molded against the die) to the final desired shape. Hence, the mold surface portion depicted at 24 in FIG. 2 need not be shaped to the precise external shape desired for the substrate. Instead, the substrate can be molded to another external shape, e.g. to only approximately the final external shape desired, and then after the molding operation, the final desired external shape can be imparted to the molded substrate as by removing portions thereof to impart the final desired shape. Of course in all cases the sprue and any flash are best removed prior to firing.

Figure 4:
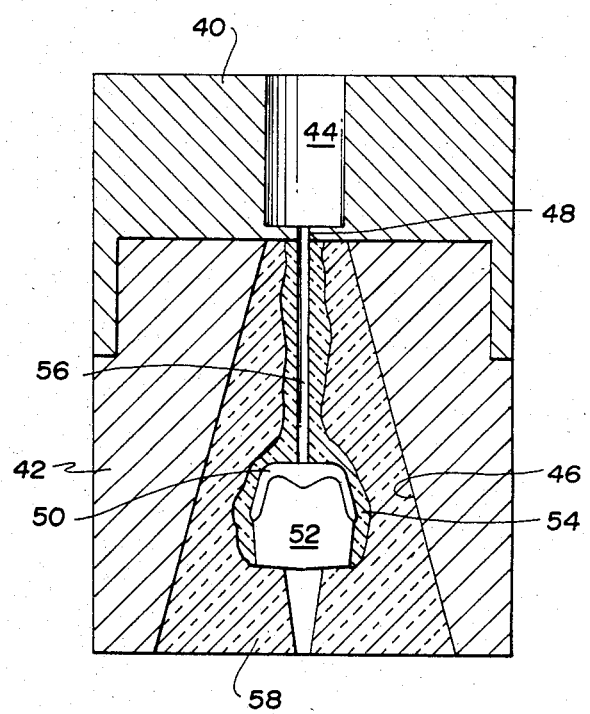
FIG. 4 is a schematic view of a modified molding apparatus for the practice of the invention.

As has been stated above, it is not necessary that the mold cavity be provided with an exit vent to allow the escape of air during the injection of the raw ceramic into the cavity. FIG. 4 shows a modified molding apparatus without an escape vent. In this apparatus, 40 and 42 are metal mold blocks which fit together as shown, the upper block 40 having a cylindrical opening 44 which communicates with the small end of a frusto conical opening 46 in the bottom mold block 42 through a passage 48. Mold cavity 50, between the die 52 and the investment material 54 which forms the female mold, is in communication with the opening 44 through a runner 56 in the investment material which is aligned with the passage 48. The die 52 is anchored in the investment material within the frusto conical opening 46. If desired the investment material 54 which forms the female surface of the mold cavity and the surface of the runner 56 can, as indicated in the drawing, be different than the investment material 58 within the remainder of the frusto conical opening. For example, the investment material 58 can, if desired, be softer or otherwise of lesser physical characteristics than the investment material 54. The die 52 is made as has been described and the mold cavity can be made as described, using a wax coping with a wax extension to provide the runner 56 upon the wax subsequently being melted or burned out after the investment. In operation a disc (not shown) of the raw shrink-free ceramic is placed in the opening 44 and, after heating, is injected into the mold cavity by a ram or plunger (not shown) in the opening 44. At the conclusion of the molding operation the investment material with the die and molded raw ceramic therein can be easily removed from the opening 46, the frusto conical shape of the opening simplifying such removal. The investment material is then removed from the die and the molded raw ceramic crown substrate removed from the investment material and the die.

After the molding operation the molded substrate, after removal of the sprue and any flash is fired to mature the ceramic as previously described. Since there is no shrinkage during the firing operation, the fired crown is of precisely the same shape and volume as prior to firing.

As a last step, generally necessary to simulate the appearance of a natural tooth, a veneer is applied to the fired substrate. This involves coating the external surfaces of the substrate with a porcelain firt or glaze and then heating to cure the veneer. It will be understood that the precise composition of the veneer will depend on the color and translucency desired for the crown, or other appliance, and the degree of color of the substrate itself. Hence, in some instances the veneer can be a transclucent glaze and in other instances, more common, it will be a white dental porcelain of the general type currently used for veneering cast metal substrates. However, in all cases it is preferred that the veneer selected have a coefficient of thermal expansion which matches or is close to that of the fired shrink-free ceramic substrate.

Figure 3:
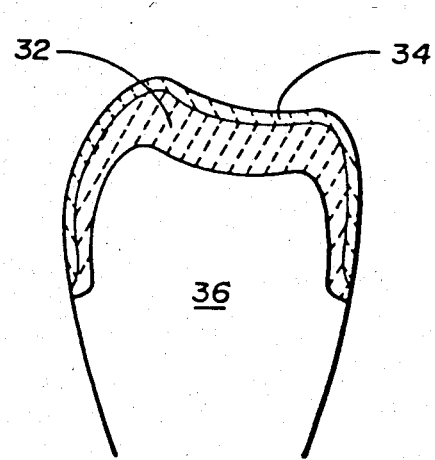
FIG. 3 is a cross sectional view of a dental appliance embodying and fabricated by the method of the present invention.

FIG. 3 is illustrative of a crown made in accordance with the invention, the crown consisting of the shrink-free ceramic substrate 32 coated with a layer of a veneer or veneers 34 and secured to the prepared tooth 36 by a thin layer of a suitable dental cement such as zinc phosphate.

It will be understood that whereas the invention has been described in its details with reference to preferred embodiments thereof, various changes and modifications may be made all within the full and intended scope of the claims which follow.

What is claimed is:

1. A method for making a custom fitted ceramic dental appliance, such as a tooth crown or bridge, to be secured to a prepared tooth, said method consisting essentially of preparing a die which is substantially a replica of the prepared tooth; molded against said die a body of raw particulate ceramic and forming said raw particulate ceramic into a compact having as an undersurface a recess substantially identical in size and shape to said die; and thereafter firing said compact to a dense monolithic body; said ceramic being of a formulation which undergoes no shrinkage during firing such that the fired body is substantially identical in size and shape to said compact prior to firing whereby said fired body fits substantially perfectly onto the prepared tooth.

2. A method as set forth in claim 1 wherein the fired body, other than the undersurface thereof, is coated with a veneer which simulates the appearance of a natural tooth and is then again fired to cure the veneer.

3. A dental appliance made by the method set forth in claim 1 or 2.

4. A method for making a custom fitted ceramic dental appliance, such as a tooth crown or bridge, to be secured to a prepared tooth, said method consisting essentially of:

preparing a die which is substantially a replica of the prepared tooth;

constructing a mold having a female mold assembled to said die thereby to provide a mold cavity between said die and said female mold;

molding a body of raw particulate ceramic in said mold cavity and forming a compact of said raw particulate ceramic having as an undersurface a recess substantially identical in shape and size to said die; and thereafter firing said compact to a hard monolithic ceramic body, said ceramic being of a formulation which undergoes no shrinkage during firing such that the fired ceramic body is substantially identical in shape and size to said compact prior to firing whereby said fired body has an undersurface which fits substantially perfectly onto the prepared tooth.

5. A method as set forth in claim 4 wherein said female mold has a shape which at least approximates that desired for the external surfaces of the appliance.

6. A method as set forth in claim 4 wherein the fired body, other than said undersurface thereof, is coated with a veneer which simulates the appearance of a natural tooth after which the body is again fired to cure the veneer.

7. A method as set forth in claim 4 wherein the die has a thin coating of a mold release agent.

8. A dental appliance made by the method set forth in claim 4, 5, 6, or 7.

9. A method for making a custom fitted ceramic dental appliance, such as a tooth crown or bridge, to be secured to a prepared tooth, said method consisting essentially of:

preparing a die which is substantially a replica of the prepared tooth;

molding against said die a body of expendable material such as wax or the like which can subsequently be easily converted to a fluid state;

molding a body of investment material against the body of expendable material while the body of expendable material remains on said die, thereby to form a female mold;

converting said body of expendable material to a fluid state to cause its removal from between said die and female mold thereby to provide a mold cavity between said die and female mold;

molding a body of raw particulate ceramic in said mold cavity and forming a compact of said raw particulate ceramic having as an undersurface a recess substantially identical in shape and size to said die; and thereafter removing said compact from said mold cavity and firing said compact to a hard monolithic ceramic body, said ceramic being of a formulation which undergoes no shrinkage during firing such that the fired ceramic body is substantially identical in shape and size to said compact prior to firing whereby said fired body has an undersurface which fits substantially perfectly onto the prepared tooth.

10. A method as set forth in claim 9 wherein the die is prepared by molding a hardenable material into an impression of the prepared tooth.

11. A method as set forth in claim 9 wherein the ceramic is an alumina ceramic and wherein the fired body, other than the undersurface thereof, is coated with a veneer which simulates the appearance of a natural tooth after which the body is again fired to cure the veneer.

12. A method as set forth in claim 1 or 9 wherein the die has a thin coating of a mold release agent.

13. A dental appliance made by the method set forth in claim 9, 10 or 11.

* * * * *